United States Patent [19]

O'Neil

[11] Patent Number: 5,013,482

[45] Date of Patent: May 7, 1991

[54] CORROSION INHIBITION

[75] Inventor: Robert M. O'Neil, Flixton, England

[73] Assignee: Ciba-Geigy Corporation, Ardsley, N.Y.

[21] Appl. No.: 381,213

[22] Filed: Jul. 17, 1989

[30] Foreign Application Priority Data

Jul. 21, 1988 [GB] United Kingdom ............... 8817381
Sep. 29, 1988 [GB] United Kingdom ............... 8822847

[51] Int. Cl.$^5$ ............................................. C023 11/10
[52] U.S. Cl. .................................. 252/395; 252/396; 422/14; 562/431; 562/471; 562/496; 562/583; 560/17; 560/61
[58] Field of Search ................. 252/395, 396; 422/14; 560/17, 61; 562/431, 471, 496, 583

[56] References Cited

U.S. PATENT DOCUMENTS

| | | | |
|---|---|---|---|
| 3,668,236 | 6/1972 | Cyba | 252/396 X |
| 3,730,485 | 5/1973 | Strange et al. | 252/396 X |
| 3,755,176 | 8/1973 | Kinney et al. | 252/48.6 |
| 3,983,171 | 9/1976 | Vanlerberghe | 562/581 |
| 4,002,676 | 1/1977 | Borggrefe | 562/583 |
| 4,153,561 | 5/1979 | Hümüller et al. | 252/8.75 |
| 4,166,132 | 8/1979 | Kraska | 514/668 |
| 4,173,665 | 11/1979 | Nia | 252/389.5 X |
| 4,219,072 | 8/1980 | Borggrefe | 165/32 |
| 4,399,043 | 8/1983 | Keil et al. | 252/8.7 |
| 4,665,017 | 5/1987 | Mifune et al. | 430/569 |
| 4,713,321 | 12/1987 | Mifune et al. | 430/569 |
| 4,713,487 | 12/1987 | Sekine et al. | 562/587 |

FOREIGN PATENT DOCUMENTS

| | | |
|---|---|---|
| 1114400 | 12/1981 | Canada . |
| 1121358 | 4/1982 | Canada . |
| 0025125 | 3/1981 | European Pat. Off. . |
| 0150930 | 8/1985 | European Pat. Off. . |
| 1224584 | 9/1966 | Fed. Rep. of Germany . |
| 1592600 | 7/1981 | Fed. Rep. of Germany . |
| 869078 | 5/1961 | United Kingdom . |
| 1566310 | 4/1980 | United Kingdom . |

OTHER PUBLICATIONS

Derwent Abstract 21778D.

Primary Examiner—Robert L. Stoll
Assistant Examiner—Valerie Fee
Attorney, Agent, or Firm—Stephen V. O'Brien

[57] ABSTRACT

The present invention provides a composition in contact with a corrodable metal surface, comprising a functional fluid and, as corrosion inhibitor, a compound having the formula I:

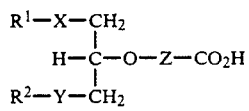

as well as salts or esters thereof, wherein $R^1$ is $C_4$-$C_{20}$ linear or branched alkyl, phenyl or $C_7$-$C_{20}$ alkylphenyl;

$R^2$ is $C_1$-$C_{12}$ linear or branched alkyl, phenyl or $C_7$-$C_{20}$ alkylphenyl, or arylalkyl containing 7-20 carbon atoms;

X is $CH_2$, O or S;

Y is O or S; and

Z is —$(CH_2)_n$— in which n is 1, 2, 3, 4 or 5, or Z is —$CH_2$—$CH(CH_3)$—.

Some of the compounds of formula I are new.

10 Claims, No Drawings

CORROSION INHIBITION

The present invention relates to corrosion inhibition and, in particular, to ether acid compounds which are active as corrosion inhibitors in functional fluids.

Many compounds or formulations are known to inhibit the corrosion of ferrous metals in contact with aqueous or partially aqueous systems. Traditionally, such corrosion inhibitors contain metals such as chromium or zinc, phosphorus in the form of phosphate, polyphosphate or phosphonate, or sodium nitrite. Most of these known corrosion inhibitors are now believed to have an adverse effect on the environment when they are discharged into waterways e.g. rivers, lakes. The known corrosion inhibitors can cause environmental damage due to their toxicity or to their tendency to promote biological growth.

Many carboxylic acid derivatives have been examined as alternative corrosion inhibitors. Generally however, high additive levels are required if carboxylic acid derivatives are to provide acceptable corrosion-inhibiting performance.

Polymeric carboxylic acids have also been described as corrosion inhibitors but again, high levels of additive are normally required.

According to the present invention, there is provided a composition in contact with a corrodable metal, preferably a ferrous metal surface, comprising a functional fluid and, as corrosion inhibitor, a compound having the formula I:

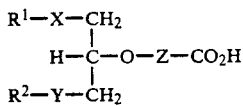

as well as salts or esters thereof, wherein
$R^1$ is $C_4$-$C_{20}$ linear or branched alkyl, phenyl or $C_7$-$C_{20}$ alkylphenyl;
$R^2$ is $C_1$-$C_{12}$ linear or branched alkyl, phenyl or $C_7$-$C_{20}$ alkylphenyl, or arylalkyl containing 7-20 carbon atoms;
X is $CH_2$, O or S;
Y is O or S; and
Z is —$(CH_2)_n$— in which n is 1, 2, 3, 4 or 5, or Z is —$CH_2$—$CH(CH_3)$—.

By the term "esters" of a compound of formula I, we mean that the $CO_2H$ group in the compound of formula I is esterified to a group of formula —$CO_2M$ in which M is $C_1$-$C_4$ alkyl optionally interrupted by one O-atom, $C_7$-$C_9$ phenylalkyl, $C_7$-$C_{18}$ alkylphenyl or $C_6$-$C_{10}$ aryl.

Salts of compounds of formula I are preferably metal-, ammonium-, or amine salts, especially salts of alkali metals, alkaline earth metals, metals of groups IIB, IIIA or VIII of the Periodic System of Elements, ammonium salts or salts of organic amines. Specific examples are sodium, potassium, calcium, magnesium, aluminium, ammonium, tri($C_1$-$C_4$) alkylammonium, bis- and tris(-hydroxyethyl)ammonium, octylamine and dodecylamine salts.

When $R^1$ is $C_4$-$C_{20}$ linear or branched alkyl it may be, e.g. n-butyl, sec.-butyl, tert.-butyl, n-pentyl, isopentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

$R^1$ or $R^2$ as $C_7$-$C_{20}$ alkylphenyl may be e.g. o-, m- or p-tolyl, -ethylphenyl, -n-propylphenyl, -n-butylphenyl, -t-butylphenyl, -n-pentylphenyl, -n-hexylphenyl, -n-heptylphenyl, tert-octylphenyl, nonylphenyl or dodecylphenyl.

$R^2$ as $C_1$-$C_{12}$ linear or branched alkyl may be e.g. methyl, ethyl, n-propyl, isopropyl, n-butyl, sec.-butyl, tert.-butyl, n-pentyl, n-hexyl, n-heptyl, n-octyl, 2-ethylhexyl, n-nonyl, n-decyl, n-undecyl or n-dodecyl.

$R^2$ as $C_7$-$C_{20}$ arylalkyl may be e.g. 1- or 2-phenylethyl, 2- or 3-phenylpropyl, or, preferably, benzyl.

Some of the compounds of formula I are known, but not for use as corrosion inhibitors in functional fluids.

For example, in GB No. 1592600, there are described, as textile conditioning agents, compounds having the formula:

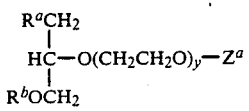

wherein
$R^a$ and $R^b$ are $C_4$-$C_8$ alkyl;
$Z^a$ is, inter alia, —$(CH_2)_xCO_2M^1$ in which x is 1, 2 or 3 and $M^1$ is e.g. alkali metal; and y is 0, 1, 2, 3 or 4.

In EP No. 23,333 textile soft rinsing agents are disclosed containing compounds having the formula:

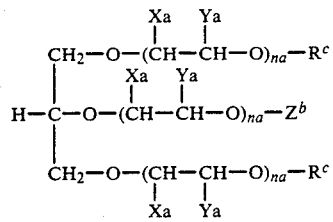

wherein
$R^c$ is inter alia $C_4$-$C_{20}$ alkyl or optionally alkyl-substituted aryl;
Xa and Ya are hydrogen or methyl but may not be simultaneously methyl; na is 0 or an integer from 1 to 20; and
$Z^b$ is e.g. —$(CH_2)_mCO_2M$ in which m is 0, 1, 2 or 3 and M is e.g. an alkali metal ion.

EP No. 144990 describes, inter alia, as silver halide solvents, thioether compounds having the formula:

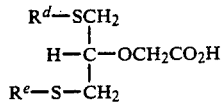

wherein $R^d$ and $R^e$, independently, are, inter alia $C_1$-$C_5$ alkyl.

Accordingly, the present invention provides new compounds having the formula IA:

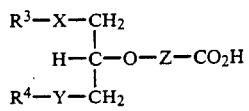

as well as salts or esters thereof, wherein $R^3$ is $C_9$–$C_{20}$ linear or branched alkyl, phenyl or $C_7$–$C_{20}$ alkylphenyl;
$R^4$ is $C_1$–$C_3$ alkyl;
and Z, X and Y have their previous significance.

Preferred compounds of formula I or IA are those wherein:
$R^1$ or $R^3$ is $C_9$–$C_{16}$ linear or branched alkyl, phenyl or $C_7$–$C_{15}$ alkylphenyl;
$R^2$ or $R^4$ is $C_1$–$C_3$ linear or branched alkyl;
X is $CH_2$, O or S;
Y is O; and
Z is —$(CH_2)_n$— in which n is 1 or 2.

Specific examples of new compounds of formula IA include:
2-(1-Methoxymethylundecyloxy)acetic acid
2-(1-Methoxymethyltridecyloxy)acetic acid
2-(1-Methoxymethylpentadecyloxy)acetic acid
3-(1-Methoxymethylundecyloxy)propanoic acid
3-(1-Methoxymethyltridecyloxy)propanoic acid
3-(1-Methoxymethylpentadecyloxy)propanoic acid
2-Carboxymethyl-1-decyl-3-methylglycerol
2-Carboxymethyl-1-dodecyl-3-methylglycerol
2-Carboxymethyl-1-tridecyl-3-methylglycerol
2-Carboxymethyl-1-tetradecyl-3-methylglycerol
2-Carboxymethyl-1-hexadecyl-3-methylglycerol
2-Carboxymethyl-1-(4-nonylphenyl)-3-methylglycerol
2-Carboxymethyl-1-(4-dodecylphenyl)-3-methylglycerol
2-(2-carboxyethyl)-1-decyl-3-methyl glycerol
2-(2-carboxyethyl)-1-dodecyl-3-methyl glycerol
2-(2-carboxyethyl)-1-tridecyl-3-methyl glycerol
2-(2-carboxyethyl)-1-tetradecyl-3-methyl glycerol
2-(2-carboxyethyl)-1-hexadecyl-3-methyl glycerol
2-(2-carboxyethyl)-1-(4-nonylphenyl)-3-methyl glycerol
2-(2-carboxyethyl)-1-(4-dodecylphenyl)-3-methyl glycerol
2-Carboxymethyl-1-methyl-3-octylthio glycerol
2-Carboxymethyl-1-methyl-3-dodecylthio glycerol
2-Carboxymethyl-1-methyl-3-hexadecylthio glycerol.

For completely aqueous systems, preferred compounds of formula I or IA are those wherein $R^1$ or $R^3$ is $C_9$–$C_{16}$ linear alkyl, $R^2$ is $C_1$–$C_3$ linear alkyl X is $CH_2$ or O, Y is O, Z is —$(CH_2)_n$— in which n is 1 or 2.

The compounds of formula I or IA may be prepared by, in a first step, reacting a compound having the formula II:

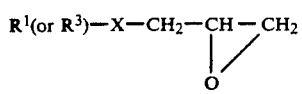   II wherein $R^1$ or $R^3$ and X have their previous significance, in the presence of a catalyst, with a compound of formula III:

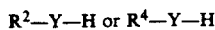   III wherein $R^2$ has its previous significance, to produce a compound of formula IV:

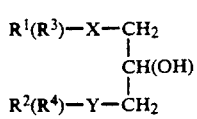   IV wherein $R^1$, $R^2$, $R^3$, $R^4$, X and Y have their previous significance.

The reaction is conveniently performed using an excess of reagent III under alkaline conditions. The catalyst may be an amine or an ion-exchange resin, but is preferably sodium metal.

The compound of formula IV is then treated with a compound V capable of converting the CH(OH) group in the compound of formula IV into a CH—O—Z—$CO_2H$ group.

Suitable compounds V include halo-carboxylic acids of formula hal—Z—$CO_2{}^-Na^+$ wherein Z has its previous significance and hal is halogen, preferably chlorine. The carboxylic acid salt so obtained may then be converted into the free acid of formula I or IA.

Alternatively, the compound of formula V may be an unsaturated nitrile, especially acrylonitrile or methacrylonitrile, which is reacted under alkaline conditions with the compound of formula IV to produce the corresponding cyano derivative, which may be hydrolysed, in conventional manner, to give a compound of formula I or IA.

Suitable epoxide starting materials of formula II include:

Epoxyalkanes 1,2-epoxyoctane
1,2-epoxydecane
1,2-epoxydodecane
1,2-epoxytetradecane
1,2-epoxyhexadecane
1,2-epoxyoctadecane
1,2-epoxyeicosane
or mixtures thereof, including commercially available mixtures containing mixed alkane moieties.

Glycidyl Ethers n-butylglycidyl ether
n-hexylglycidyl ether
n-octylglycidyl ether
i-octylglycidyl ether
n-decylglycidyl ether
n- or iso dodecyl glycidyl ether
n- or iso tridecyl glycidyl ether
n- or iso tetradecyl glycidyl ether
n- or iso pentadecyl glycidyl ether
n- or iso hexadecyl glycidyl ether
n- or iso octadecyl glycidyl ether
n- or iso eicosyl glycidyl ether
phenyl glycidyl ether
o-cresyl glycidyl ether
m-cresylglycidyl ether
p-cresylglycidyl ether
4-sec butylphenyl glycidyl ether
4-tert butylphenyl glycidyl ether
4-tert octylphenyl glycidyl ether
4-nonylphenyl glycidyl ether
4-dodecylphenyl glycidyl ether
or mixtures thereof such as "Epoxide 8", a commercially available mixture of $C_{12}$ and $C_{14}$ glycidyl ethers supplied by Procter and Gamble.

Glycidyl Thioethers n-butylglycidyl thioether
tert-butylglycidyl thioether
iso-octylglycidyl thioether
tert-octylglycidyl thioether
iso-nonylglycidyl thioether n-dodecylglycidyl thioether
iso-dodecylglycidyl thioether
tert-dodecylglycidyl thioether
n-hexadecylglycidyl thioether
tert-hexaglycidyl thioether
phenyl glycidyl thioether
or mixtures there, including commercially available mixtures comprising mixed alkane moieties.

Suitable alcohol reactants $R^2$—Y—H or $R^4$—Y—H of formula III include: methanol, ethanol, 1-propanol, 2-propanol, 1-butanol, 2-butanol, isobutylalcohol, tert butylalcohol, 1-pentanol, isoamylalcohol, 1-hexanol, 2-hexanol, 1-heptanol, 2-heptanol, 1-octanol, 2-octanol, 2-ethylhexanol, 1-nonanol, 2-nonanol, 1-decanol, 2-decanol, 1-undecanol, 2-undecanol, phenol, o-cresol, p-cresol, m-cresol, 4-sec-butylphenol, 4-tert-butylphenol, 4-tert-octylphenol, 4-nonylphenol and 4-dodecylphenol.

Suitable mercaptans $R^2$—Y—H or $R^4$—Y—H of formula III include:
methane thiol
ethane thiol
1-mercaptopropane
2-mercaptopropane
1-mercaptobutane
2-mercaptobutane
t-butyl mercaptan
1-mercaptohexane
2-mercaptohexane
1-mercaptooctane
t-octylmercaptan
1-mercaptononane
t-nonylmercaptan
1-mercaptodecane
1-mercaptododecane
tert-dodecylmercaptan
thiophenol
thiocresol.

Any amount of the compound of formula I, or mixture thereof, which is effective as a corrosion inhibitor in the composition according to the invention can be used, but the amount expediently ranges from 0.0001 to 5% by weight, preferably from 0.001 to 3% by weight and especially preferred from 0.01 to 2% by weight, based on the total weight of the functional fluid base.

The functional fluid base for the compositions of the present invention is either (a) an aqueous-based system or (b) an oil-based system.

Examples of systems which may provide the base for the compositions according to the present invention include functional fluids such as lubricants e.g. those having a mineral oil, poly-alpha olefin or synthetic carboxylic acid ester base; hydraulic fluids e.g. those based on mineral oils, phosphate esters, aqueous polyglycol/-polyglycol ether mixtures or glycol systems; oil-in-water or water-in-oil systems; metal-working fluids having, as their base, mineral oil for aqueous systems; water- or aqueous glycol- or ethylene- or propylene glycol/methanol based engine coolant systems; transformer- or switch oils; as well as aqueous systems e.g. industrial cooling water; aqueous air-conditioning systems; steam-generating systems; sea-water evaporator systems; hydrostatic cookers; and aqueous closed circuit heating or refrigerant systems.

When a functional fluid system is a synthetic lubricant, examples thereof include lubricants based on a diester of a dibasic acid and a monohydric alcohol, for instance dioctyl sebacate or dinonyladipate; on a triester of trimethylol-propane and a monobasic acid or mixture of such acids, for instance trimethylol propane tripelargonate, trimethylolpropane tricaprylate or mixtures thereof; on a tetraester of pentaerythritol and a monobasic acid or mixture of such acids, for instance pentaerythritol tetracaprylate; or on complex esters derived from monobasic acid, dibasic acids and polyhydric alcohols, for instance a complex ester derived from trimethylol propane, caprylic acid and sebacic acid; or of mixtures thereof.

Other synthetic lubricants are those known to the art-skilled and described e.g. in "Schmiermittel-Taschenbush" (Huethig Verlag, Heidelberg 1974). Especially suitable, apart from the preferred mineral oils are e.g. phosphates, glycols, polyglycols, polyalkylene glycols and poly-alpha olefins.

In order to improve various applicational properties, a functional fluid composition of the invention may also contain other additives such as, for oil-based systems, one or more of antioxidants, metal deactivators, further corrosion or rust inhibitors, viscosity-index improvers, pour-point depressants, dispersants/surfactants or anti-wear additives; and for aqueous-based systems, one or more of antioxidants, other corrosion- and rust inhibitors, metal deactivators, extreme pressure- or anti-wear buffering agents and anti-foams.

For oil-based systems, examples of other additives are:

Examples of phenolic antioxidants

1. Alkylated Monophenols 2,6-Di-tert.-butylphenol
2-tert.-butyl-4,6-dimethylphenol
2,6-di-tert.-butyl-4-ethylphenol
2,6-di-tert.-butyl-4-n-butylphenol
2,6-di-tert.-butyl-4-i-butylphenol
2,6-di-cyclopentyl-4-methylphenol
2-($\beta$-methylcyclohexyl)-4,6-dimethylphenol
2,6-di-octadecyl-4-methylphenol
2,4,6-tri-cyclohexylphenol
2,6-di-tert.-butyl-4-methoxymethylphenol 2. Alkylated Hydroquinones 2,6-Di-tert.-butyl-4-methoxyphenol
2,5-di-tert.-butyl-hydroquinone
2,5-di-tert.-amyl-hydroquinone
2,6-diphenyl-4-octadecyloxyphenol 3. Hydroxylated Thiodiphenylethers 2,2'-Thio-bis-(6-tert.-butyl-4-methylphenol)
2,2'-thio-bis-(4-octylphenol)
4,4'-thio-bis-(6-tert.-butyl-3-methylphenol)
4,4'-thio-bis-(6-tert.-butyl-2-methylphenol)

4. Alkylidene-Bisphenols 2,2'-Methylene-bis-(6-tert.-butyl-4-methylphenol)
2,2'-methylene-bis-(6-tert.-butyl-4-ethylphenol)
2,2'-methylene-bis-(4-methyl-6-($\alpha$-methylcyclohexyl)-phenol)
2,2'-methylene-bis(4-methyl-6-cyclohexylphenol)
2,2'-methylene-bis-(6-nonyl-4-methylphenol)
2,2'-methylene-bis-(4,6-di-tert.-butylphenol)
2,2'-ethylidene-bis-(4,6-di-tert.-butylphenol)
2,2'-ethylidene-bis-(6-tert.-butyl-4-isobutylphenol)
2,2'-methylene-bis-(6-($\alpha$-methylbenzyl-4-nonylphenol)
2,2'-methylene-bis-(6-($\alpha,\alpha$-dimethylbenzyl)-4-nonylphenol)

4,4'-methylene-bis-(6-tert.-butyl-2-methylphenol)
1,1'-bis-(5-tert.-butyl-4-hydroxy-2-methylphenol)-butane
2,6-di-(3-tert.-butyl-5-methyl-2-hydroxybenzyl)-4-methylphenol
1,1,3-tris-(5-tert.-butyl-4-hydroxy-2-methylphenol)-3-n-dodecyl)-mercaptobutane
ethyleneglycol-bis-[3,3-bis-(3'-tert.-butyl-4'-hydroxyphenol)-butyrate]
di-(3-tert.-butyl-4-hydroxy-5-methylphenyl)-dicyclopentadiene
di-[3'-tert.-butyl-2'-hydroxy-5'-methyl-benzyl)-6-tert.-butyl-4-methyl-phenyl]terephthalate

5. Benzyl Compounds 1,3,5-Tri-(3,5-di-tert.-butyl-4-hydroxybenzyl)-2,4,6-trimethyl-benzene
di-(3,5-di-tert.-butyl-4-hydroxybenzyl)-sulphide
bis-(4-tert.-butyl-3-hydroxy-2,6-dimethylbenzyl)dithiol-terephthalate
1,3,5-tris-(3,5-di-tert.-butyl-4-hydroxybenzyl)-isocyanurate
1,3,5-tris-(4-tert.-butyl-3-hydroxy-2,6-dimethylbenzyl)-isocyanurate
3,5-di-tert.-butyl-4-hydroxybenzyl-phosphonic acid-dioctadecylester
3,5-di-tert.-butyl-4-hydroxybenzyl-phosphonic acid-monoethylester calcium salt

6. Acylaminophenols

4-Hydroxy-lauric acid anilide
4-Hydroxy-stearic acid anilide
2,4-bis-octylmercapto-6-(3,5-di-tert.-butyl-4-hydroxyanilino)-s-triazine
N-(3,5-di-tert.-butyl-4-hydroxyphenyl)-carbamic acid octyl ester

| 7. Esters of β-(3,5-Di-tert.-butyl-4-hydroxyphenol)-propionic acid with mono- or polyhydric alcohols e.g. with | |
|---|---|
| methanol | diethyleneglycol |
| octadecanol | triethyleneglycol |
| 1,6-hexanediol | pentaerythritol |
| neopentylglycol | tris-hydroxyethyl-isocyanurate |
| thiodiethyleneglycol | bis-hydroxyethyl-oxalic acid diamide |

| 8. Esters of β-(5-tert.-butyl-4-hydroxy-3-methylphenyl)-propinic acid | |
|---|---|
| methanol | diethyleneglycol |
| octadecanol | triethyleneglycol |
| 1,6-hexanediol | pentaerythritol |
| neopentylglycol | tris-hydroxyethyl-isocyanurate |
| thiodiethyleneglycol | di-hydroxyethyl-oxalic acid diamide |

9. Amides of β-(3,5-Di-tert.-butyl-4-hydroxyphenyl)-propionic acid e.g.

N,N'-Di-(3,5-di-tert.-butyl-4-hydroxyphenylpropionyl)-hexamethylene-diamine
N,N'-Di-(3,5-di-tert.-butyl-4-hydroxyphenylpropionyl)-trimethylene-diamine
N,N'-Di-(3,5-di-tert.-butyl-4-hydroxyphenylpropionyl)-hydrazine

Examples of amine antioxidants

N,N'-Di-isopropyl-p-phenylenediamine
N,N'-di-sec.-butyl-p-phenylenediamine
N,N'-bis(1,4-dimethyl-pentyl)-p-phenylenediamine
N,N'-bis(1-ethyl-3-methyl-pentyl)-p-phenylenediamine
N,N'-bis(1-methyl-heptyl)-p-phenylenediamine
N,N'-dicyclohexyl-p-phenylenediamine
N,N'-diphenyl-p-phenylenediamine
N,N'-di-(naphthyl-2)-p-phenylenediamine
N-isopropyl-N'-phenyl-p-phenylenediamine
N-(1,3-dimethyl-butyl)-N'-phenyl-p-phenylenediamine
N-(1-methyl-heptyl)-N'-phenyl-p-phenylenediamine
N-cyclohexyl-N'-phenyl-p-phenylenediamine
4-(p-toluene-sulfonamido)-diphenylamine
N,N'-dimethyl-N,N'-di-sec.-butyl-p-phenylenediamine
diphenylamine
4-isopropoxy-diphenylamine
N-phenyl-1-naphthylamine
N-phenyl-2-naphthylamine
octylated diphenylamine
octylated N-phenyl-α-(or)β-naphthylamine
4-n-butylaminophenol
4-butyrylamino-phenol
4-nonanoylamino-phenol
4-dodecanoylamino-phenol
4-isodecanoylamino-phenol
4-octadecanoylamino-phenol
di-(4-methoxy-phenyl)-amine
2,6-di-tert.-butyl-4-dimethylamino-methyl-phenol
2,4'-diamino-diphenylmethane
4,4'-diamino-diphenylmethane
N,N,N'N'-tetramethyl-4,4'-diamino-diphenylmethane
1,2-di-(phenylamino)-ethane
1,2-di-[2-(methyl-phenyl)-amino]-ethane
1,3-di-(phenylamino)-propane
(o-tolyl)-biguanide
di-[4-(1',3'-dimethyl-butyl)-phenyl]amine Examples of metal passivators are: for copper e.g.

Benzotriazole, tolutriazole, 1,2,4-triazole and derivatives thereof, tetra-hydrobenzotriazole, 2-mercaptobenzothiazole, 2,5-dimercapto-thiadiazole, salicylidene-propylenediamine and salts of salicylaminoguanidine.

Examples of rust inhibitors are:

(a) Organic acids, their esters, metal salts and anhydrides, e.g. N-oleoyl-sarcosine, sorbitan-mono-oleate, lead-naphthenate, dodecenyl-succinic acid (and its partial esters and amides), 4-nonyl-phenoxy-acetic acid.

(b) Nitrogen-containing compounds e.g.

I. Primary, secondary or tertiary aliphatic or cycloaliphatic amines and amine-salts or organic and inorganic acids, e.g. oil-soluble alkyl-ammonium carboxylates II. Heterocyclic compounds e.g. substituted imidazolines and oxazolines (c) Phosphorus-containing compounds e.g. amino salts of phosphonic acid or acid partial esters, zinc dialkyldithio phosphates (d) Sulphur-containing compounds e.g. barium-dinonylnaphthalene-n-sulphonates, calcium petroleum sulfonates Examples of viscosity-index improvers are e.g.

Polymethacrylates, vinylpyrrolidone/methacrylate-copolymers, polybutenes, olefin-copolymers styrene/acrylate-copolymers.

Examples of pour-point depressants are e.g.

Polymethacrylates, or alkylated naphthalene derivatives.

Examples of dispersants/surfactants are e.g.

Polybutenylsuccinic acid-amides or -imides, polybutenylphosphonic acid derivatives, basic magnesium-, calcium- and barium sulphonates and -phenolates.

Examples of anti-wear additives are e.g.

Sulphur- and/or phosphorus- and/or halogen-containing compounds e.g. sulphurised vegetable oils, zinc dialkyldithiophosphates, tritolylphosphate, chlorinated paraffins, alkyl- and aryldisulphides.

For functional fluid bases which are completely aqueous, such as cooling water systems, air-conditioning systems, steam-generating systems, sea-water evaporator systems, hydrostatic cookers, and closed circuit heating or refrigerant systems, further corrosion inhibitors may be used such as, for example, water soluble zinc salts; phosphates; polyphosphates; phosphonic acids and their salts, for example, hydroxyethyldiphosphonic acid (HEDP), nitrilotris methylene phosphonic acid and methylamino dimethylene phosphonocarboxylic acids and their salts, for example, those described in German Offenlegungsschrift No. 2632774, hydroxyphosphonoacetic acid, 2-phosphonobutane-1,2,4-tricarboxylic acid and those disclosed in GB No. 1572406; nitrates, for example sodium nitrate; nitrites e.g. sodium nitrite; molybdates e.g. sodium molybdate; tungstates, silicates e.g. sodium silicate; benzotriazole, bis-benzotriazole or copper deactivating benzotriazole or tolutriazole derivatives or their Mannich base derivatives; mercaptobenzothiazole; N-acyl sarcosines; N-acylimino diacetic acids; ethanolamines; fatty amines; and polycarboxylic acids, for example, polymaleic acid and polyacrylic acid, as well as their respective alkali metal salts, copolymers of maleic anhydride, e.g. copolymers of maleic anhydride and sulphonates styrene, copolymers or acrylic acid e.g. copolymers or acrylic acid and hydroxyalkylated acrylic acid, and substituted derivatives of polymaleic and polyacrylic acids and their copolymers. Moreover, in such completely aqueous systems, the corrosion inhibitor according to the invention may be used in conjunction with dispersing and/or threshold agents e.g. polymerised acrylic acid (or its salts), phosphino-polycarboxylic acid (as described and claimed in British Patent No. 1548235), the cotelomeric compounds described in European Patent Application No. 0150706, hydrolysed polyacrylonitrile, polymerised methacrylic acid and its salts, polyacrylamide and copolymers thereof from acrylic and methacrylic acids, lignin sulphonic acid and its salts, tannin, naphthalene sulphonic acid/formaldehyde condensation products, starch and its derivatives, cellulose, acrylic acid/lower alkyl hydroxyacrylate copolymers e.g. those described in U.S. Pat. No. 4,029,577, styrene/maleic anhydride copolymers and sulfonated styrene homopolymers e.g. those described in U.S. Pat. No. 4,374,733 and combinations thereof. Specific threshold agents, such as for example, 2-phosphono-butane-1,2,4-tricarboxylic acid (PBSAM), hydroxyethyldiphosphonic acid (HEDP), hydrolysed polymaleic anhydride and its salts, alkyl phosphonic acid, hydroxyphosphonoacetic acid, 1-aminoalkyl-1,1-diphosphonic acids and their salts, and alkali metal poly-phosphates, may also be used.

Particularly interesting additive packages are those comprising compounds of formula I with one or more of polymaleic acid or polyacrylic acid or their copolymers, and/or HEDP and/or PBSAM and/or triazoles e.g. tolutriazole.

Precipitating agents such as alkali metal orthophosphates, carbonates; oxygen scavengers such as alkali metal sulphites and hydrazines; sequestering agents such as nitrilotriacetic acid and its salts; anti-foaming agents such as silicones e.g. polydimethylsiloxanes, distearyl-sebacamides, distearyl adipamide and related products derived from ethylene oxide and/or propylene oxide condensations, in addition to fatty alcohols, such as capryl alcohols and their ethylene oxide condensates; and biocides e.g. amines, quaternary ammonium compounds, chlorophenols, sulphur-containing compounds such as sulphones, methylene bis thio-cyanates and carbamates, isothiazolones, brominated propionamides, triazines, phosphonium compounds, chlorine and chlorine-release agents and organo-metallic compounds such as tributyl tin oxide, may be used.

The functional fluid base may be partly aqueous e.g. in aqueous machining fluid formulation, e.g. a water dilutable cutting or grinding fluid.

The aqueous machining fluid formulations according to the invention may be e.g. metal working formulations. By "metal working" we mean reaming, broaching, drawing, spinning, cutting, grinding, boring, milling, turning, sawing, non-cutting shaping, rolling or quenching. Examples of water-dilutable cutting or grinding fluids into which the corrosions inhibiting compound may be incorporated include:

(a) Aqueous concentrates of one or more corrosion inhibitors, and optionally one or more anti-water additives which are usually employed as grinding fluids;

(b) Polyglycols containing biocides, corrosion inhibitors and anti-wear additives for cutting operations or grinding;

(c) Semi-synthetic cutting fluids similar to (b) but containing in addition 10 to 25% oil with sufficient emulsifier to render the water diluted product translucent;

(d) An emulsifiable mineral oil concentrate containing, for example, emulsifiers, corrosion inhibitors, extreme pressure/anti-wear additives, biocides, anti-foaming agents, coupling agents etc; they are generally diluted with water to a white opaque emulsion;

(e) A product similar to (d) containing less oil and more emulsifier which on dilution gives a translucent emulsion for cutting or grinding operations.

For those partly-aqueous systems in which the functional fluid is an aqueous machining fluid formulation the inhibitor of formula I may be used singly, or in admixture with other additives e.g. known further corrosion inhibitors or extreme-pressure additives.

Examples of other corrosion inhibitors which may be used in these partly aqueous systems, in addition to the compound of formula I used according to the invention, include the following groups:

(a) Organic acids, their esters or ammonium, amine, alkanolamine and metal salts, for example, benzoic acid, p-tert.-butyl benzoic acid, disodium sebacate, triethanolamine laurate, iso-nonanoic acid, triethanolamine salt of p-toluene sulphonamide caproic acid, triethanolamine salt of benzene sulphonamide caproic acid, triethanolamine salts of 5-ketocarboxylic acid derivatives as described in European Patent No.

41927, sodium N-lauroyl sarcosinate or nonyl phenoxy acetic acid;
(b) Nitrogen containing materials such as the following types: fatty acid alkanolamides; imidazolines, for example, 1-hydroxyethyl-2-oleyl-imidazolines; oxazolines; triazoles for example, benzotriazoles; or their Mannich base derivatives; triethanolamines; fatty amines, inorganic salts, for example, sodium nitrate; and the carboxy-triazine compounds described in European Patent No. 46139;
(c) Phosphorus containing materials such as the following types: amine phosphates, phosphonic acids or inorganic salts, for example, sodium dihydrogen phosphate or zinc phosphate;
(d) Sulphur containing compounds such as the following types: sodium, calcium or barium petroleum sulphonates, or heterocyclics, for example, sodium mercaptobenzothiazole. Nitrogen containing materials, particularly triethanolamine, are preferred.

The following Examples further illustrate the present invention. Percentages and parts are by weight unless otherwise stated.

EXAMPLE 1

2-Carboxymethyl-1-isooctyl-3-methyl glycerol

Sodium metal (2.3 g; 0.1 mole) is dissolved in methanol (160 g; 5 moles). The solution is heated to reflux and treated dropwise over 2 hours with isooctyl glycidyl ether (186 g; 1 mole). After complete addition, the reaction mixture is maintained under reflux conditions for a further 6 hours. After cooling to ambient temperature, the reaction mixture is treated with acetic acid (5.8 g; 0.1 mole) and then the excess solvent is removed under vacuum. The oily residue is treated with water (250 ml) and then extracted with ether (250 ml). The ether extract is dried over $MgSO_4$, filtered and evaporated. The residue is distilled under vacuum to yield 1-isooctyl-3-methyl glycerol, as a colourless oil, bp 75°–80° C./0.07 mbar, yield 145.6 g (67%).

109 g (0.5 mole) of 1-isooctyl-3-methyl glycerol obtained as above are stirred vigorously with sodium chloroacetate (58.3 g; 0.5 mole) at 40°–50° C. and treated portionwise over 3 hours with powdered sodium hydroxide (20 g; 0.5 mole). After complete addition, the reaction mixture is stirred for a further 6 hours at 40°–50° C. The reaction mixture is then treated with 10% $H_2SO_4$ to adjust the pH to 2 and, after heating to 80° C., two layers are formed. The upper organic layer is separated, treated with water (200 ml) and extracted with ether. The ether extract is washed with water then dried over $MgSO_4$. The filtered extract is evaporated and the residue is distilled under vacuum to yield 2-carboxymethyl-1-isooctyl-3-methyl glycerol, as a colourless oil, bp. 136°–140° C./0.07 mbar, yield=93.8 g (68%).

Analysis: Found: C 61.23%; H 10.55%. $C_{14}H_{28}O_5$ requires: C 60.84%; H 10.21%.

EXAMPLE 2

2-(1-(Methoxymethylundecyloxy)acetic acid 1,2-Epoxydodecane is reacted with sodium in methanol as in Example 1 to yield 1-methoxy-2-dodecanol as a colourless oil, bp 97° C./0.07 mbar, yield 88%.

108 g (0.5 mole) 1-methoxy-2-dodecanol are reacted with sodium chloroacetate (58.3 g; 0.5 mole) and powdered sodium hydroxide (20 g; 0.5 mole) as in Example 1 to yield 2-(1-Methoxymethylundecyloxy)acetic acid as a colourless oil, bp. 162° C./0.26 mbar, yield 59.0 g (43%).

Analysis: Found: C 66.05%; H 11.42%. $C_{15}H_{30}O_4$ requires: C 65.65%; H 11.02%.

EXAMPLE 3

2-Carboxymethyl-1-methyl-3-tertnonylthio glycerol tert-Nonylthioglycidyl ether is reacted with sodium in methanol as in Example 1 to yield 1-methoxy-3-tert-nonylthioglycerol as a colourless oil, bp 106°–110° C./0.26 mbar, yield 81%.

74.4 g (0.3 mole) tertnonylthioglycerol are reacted with sodium chloroacetate (46.4 g; 0.3 mole) and powdered sodium hydroxide as in Example 1 to yield 2-carboxymethyl-1-methyl-3-tert-nonylthioglycerol as a colourless oil, bp 195° C./0.07 mbar, yield 36%. Satisfactory infrared and nmr spectra are obtained for the title product.

EXAMPLES 4 TO 19

Using methods analogous to that set out in Example 1, compounds having the formula:

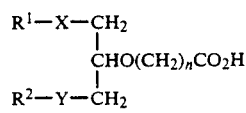

are prepared.

| Example | $R^1$ | $R^2$ | X | Y | n | bp |
|---|---|---|---|---|---|---|
| 4 | $C_8H_{17}$ | $C_8H_{17}$ | O | O | 1 | 184° C./0.07 mbar |
| 5 | $C_{10}H_{21}$ | $C_{10}H_{21}$ | O | O | 1 | 215° C./0.07 mbar |
| 6 | $C_{12}H_{25}$ | $C_{12}H_{25}$ | O | O | 1 | undistilled oil |
| 7 | $C_{12}H_{25}/C_{14}H_{29}$ mixture | $CH_3$ | O | O | 1 | 195–205° C./0.26 mbar |
| 8 | $C_{12}H_{25}$ | $C_4H_9$ | O | O | 1 | 207° C./0.13 mbar |
| 9 | $^iC_{12}H_{25}$ | $CH_3$ | S | O | 1 | 210° C./0.10 mbar |
| 10 | $C_{10}H_{21}$ | $CH_3$ | $CH_2$ | O | 1 | 174° C./0.07 mbar |
| 11 | $C_6H_5$ | $CH_3$ | O | O | 1 | 185° C./0.40 mbar |
| 12 | $C_9H_{19}$ (60% meta 40% para)-phenyl | $CH_3$ | O | O | 1 | 212° C./0.07 mbar |
| 13 | $C_{12}H_{25}/C_{13}H_{27}$ | $CH_3$ | O | O | 1 | 200–216° C./0.4 mbar |
| 14 | $C_6H_{13}$ | $C_4H_9$ | O | O | 1 | 154° C./0.08 mbar |
| 15 | $C_4H_9$ | $C_4H_9$ | O | O | 1 | 142° C./0.08 mbar |
| 16 | $^iC_4H_9$ | $^nC_4H_9$ | S | O | 1 | 146° C./0.04 mbar |
| 17 | $C_{12}H_{25}$ | $CH_3$ | O | O | 1 | 180° C./0.02 mbar |
| 18 | $C_{13}H_{27}$ | $CH_3$ | O | O | 1 | 180° C./0.02 mbar |
| 19 | $C_{14}H_{29}$ | $CH_3$ | O | O | 1 | 190° C./0.03 mbar |

EXAMPLES 20 TO 33

Corrosion Inhibition in oils

Several of the products used according to the present invention are tested as rust inhibitors in a turbine grade oil of viscosity 26.2 $mm^2/s$ at 40° C., 4.8 $mm^2/s$ at 100° C. and sulphur content of 0.54%, using the ASTM D665B method. The test results are expressed in the following manner Rating 0—No rust or traces of rust on test spindle
1—Rusting confined to not more than 6 spots, each of which is 1 mm or less in diameter 2—Rusting in excess of the above but confined to less than 5% of the surface of the spindle
3—Rusting covering more than 5% of the surface of the spindle

| Example | Corrosion Inhibitor Product of Example | Concentration | ASTM D665B rating |
|---|---|---|---|
| — | none (control) | — | 3 |
| 20 | 1 | 0.05% | 0 |
| 21 | 2 | 0.05% | 0 |
| 22 | 3 | 0.05% | 0 |
| 23 | 4 | 0.05% | 0 |
| 24 | 5 | 0.05% | 0 |
| 25 | 6 | 0.05% | 2 |
| 26 | 7 | 0.05% | 0 |
| 27 | 8 | 0.05% | 0 |
| 28 | 9 | 0.05% | 1 |
| 29 | 10 | 0.05% | 0 |
| 30 | 12 | 0.05% | 0 |
| 31 | 13 | 0.05% | 0 |
| 32 | 17 | 0.05% | 0 |
| 33 | 19 | 0.05% | 0 |

EXAMPLES 34 TO 42

Corrosion Inhibitor in metal working fluid

Several of the products used according to the present invention are tested as rust inhibitors in aqueous cutting fluid using the IP287 chip/filter paper method. One percent solutions of the products are prepared in DIN 51360 water in the form of their triethanolamine salts and the test results are expressed in the following manner.

Rating

0—No corrosion
1—maximum of 3 corrosion spots each of which is less than 1 mm in diameter
2—Not more than 1% of the surface stained
3—Above 1% but below 5% of the surface stained
4—Above 5% of the surface stained

| Example | Corrosion Inhibitor Product of Example | pH | IP 287 Rating |
|---|---|---|---|
| — | none (control) | 9.0 | 4 |
| 34 | 1 | 9.0 | 0 |
| 35 | 2 | 9.0 | 0 |
| 36 | 4 | 9.0 | 0 |
| 37 | 7 | 9.0 | 0 |
| 38 | 10 | 9.0 | 0 |
| 39 | 11 | 9.0 | 2 |
| 40 | 14 | 9.0 | 0 |
| 41 | 15 | 9.0 | 0 |
| 42 | 16 | 9.0 | 0 |

EXAMPLES 43 TO 48

Corrosion Inhibition in Cooling Water

Several of the products used according to the present invention are tested as corrosion inhibitors by a rotating coupon test in the following corrosive water:

| | |
|---|---|
| pH | 7.0 |
| pA | 0 |
| TA | 20 |
| TH | 75 |
| $Ca^{2+}$ (ppm) | 50 |
| $Mg^{2+}$ (ppm) | 25 |
| $Cl^-$ (ppm) | 20 |
| $SO_4^{2-}$ (ppm) | 20 |

In a 1 liter reservoir of the test water, two pre-cleaned and pre-weighed mild steel coupons are rotated at a coupon velocity of 61 cms per second. The test is conducted over 48 hours in oxygenated water at 40° C. using 20 ppm in examples 43 to 45 and 15 ppm in examples 46 to 48 of the appropriate concentration of corrosion inhibitor.

The coupons are removed, scrubbed, immersed for one minute in hydrochloric acid inhibited with 1% by weight of hexamine and then rinsed, dried and re-weighed. A certain loss in weight will have occurred. A blank test i.e. immersion of mild steel specimen in the test water in the absence of any potential corrosion inhibitor, is carried out with each series of tests. The corrosion rates are calculated in milligrams of weight loss/sq. decimeter/day (m.d.d.). The results obtained in a series of tests are set out in the following Table.

| Example | Corrosion Inhibitor Product of Example | Concentration (ppm) | Corrosion rate (m.d.d.) |
|---|---|---|---|
| — | Blank | — | 275.8 |
| 43 | 7 | 20 | 7.0 |
| 44 | 2 | 20 | 12.1 |
| 45 | 10 | 20 | 7.7 |
| 46 | 17 | 15 | 15.0 |
| 47 | 18 | 15 | 7.0 |
| 48 | 19 | 15 | 7.0 |

What is claimed is:

1. A method of protecting a metal surface against corrosion comprising contacting the metal surface with a functional fluid containing an effective corrosion inhibiting amount of a compound of the formula I:

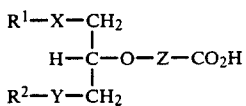

as well as salts or esters thereof, wherein
$R^1$ is $C_4$-$C_{20}$ linear or branched alkyl, phenyl or $C_7$-$C_{20}$alkylphenyl;
$R^2$ is $C_1$-$C_{12}$ linear or branched alkyl, phenyl or $C_7$-$C_{20}$alkylphenyl, or arylalkyl containing 7-20 carbon atoms;
X is $CH_2$, O or S;
Y is O or S; and
Z is —$(CH_2)_n$— in which n is 1, 2, 3, 4 or 5, or Z is —$CH_2$—$CH(CH_3)$—.

2. Method according to claim 1 wherein
$R^1$ is $C_9$-$C_{16}$ linear or branched alkyl, phenyl or $C_7$-$C_{15}$alkylphenyl;
$R^2$ is $C_1$-$C_3$ linear or branched alkyl;
X is $CH_2$, O or S;
Y is O; and
Z is —$(CH_2)$— or —$(CH_2)_2$—.

3. Method according to claim 1 wherein the metal surface is a ferrous metal surface.

4. Method according to claim 1 wherein the amount of the compound of formula I ranges from 0.0001 to 5% by weight, based on the total weight of the functional fluid.

5. Method according to claim 1 wherein the functional fluid is oil-based.

6. Method according to claim 5 wherein the fluid also contains one or more antioxidants, metal deactivators, further corrosion or rust inhibitors, viscosity-index improvers, pour-point depressants, dispersants/surfactants or anti-wear additives.

7. Method according to claim 1 wherein the functional fluid is completely aqueous.

8. Method according to claim 7 wherein the fluid also contains one or more further corrosion inhibitors, dispersing and/or threshold agents, precipitating agents, oxygen scavengers, sequestering agents, antifoaming agents or biocides.

9. Method according to claim 1 wherein the functional fluid is partly aqueous.

10. Method according to claim 9 wherein the fluid also contains one or more further corrosion inhibitors or extreme-pressure additives.

* * * * *